United States Patent [19]

Hennemuth et al.

[11] Patent Number: 4,529,397

[45] Date of Patent: Jul. 16, 1985

[54] CARDIOPLEGIC CONTROLLING AND REGULATING SYSTEM

[75] Inventors: Kurt Hennemuth, Northeim; Heinz G. Köhn, Dransfeld; Erich Knothe, Bovenden; Günter Pradel, Göttingen, all of Fed. Rep. of Germany

[73] Assignee: Sartorius GmbH, Fed. Rep. of Germany

[21] Appl. No.: 460,483

[22] Filed: Jul. 24, 1983

[30] Foreign Application Priority Data

Feb. 9, 1982 [DE] Fed. Rep. of Germany ....... 3204317

[51] Int. Cl.³ .............................................. A61M 1/03
[52] U.S. Cl. .......................................... 604/4; 604/27; 604/30
[58] Field of Search ..................... 604/4, 27–29, 604/6, 53, 56, 83; 128/DIG. 3; 210/927, 650, 651

[56] References Cited

U.S. PATENT DOCUMENTS

| | | | |
|---|---|---|---|
| 3,579,441 | 5/1971 | Brown | 604/4 |
| 3,881,483 | 5/1975 | Sausse | 604/4 |
| 4,096,859 | 6/1978 | Agarwal et al. | 604/28 |
| 4,190,047 | 2/1980 | Jacobsen et al. | 604/28 |
| 4,249,923 | 2/1981 | Walda | 604/113 |
| 4,401,431 | 8/1983 | Arp | 604/4 |
| 4,416,280 | 11/1983 | Carpenter et al. | 604/4 |

FOREIGN PATENT DOCUMENTS

| | | | |
|---|---|---|---|
| 2755214 | 6/1979 | Fed. Rep. of Germany | 604/29 |
| 2471194 | 6/1981 | France | 604/4 |
| 1537444 | 12/1978 | United Kingdom | 604/4 |

Primary Examiner—Stephen C. Pellegrino
Assistant Examiner—Michelle N. Lester
Attorney, Agent, or Firm—Eric P. Schellin

[57] ABSTRACT

A cardioplegic controlling and regulating device for the dosed perfusion of cardioplegic perfusion solution in open-heart surgery has a storage container for receiving the cardioplegic solution, which container is part of a scale and can be connected to the heart over a tubular conduit. A pressure-controlled dosing pump which acts on the tubular conduit and cooperates with a second, reversible pump which is constructed as an exhaust pump and is selectively operable synchronously or asynchronously within controllable tolerance limits with the first dosing pump during the perfusion and sustaining of the perfusion. An ultrafilter for the mixture of blood and cardioplegic solution removed from the patient's heart is located in a removal line. An outlet for the blood separated form the ultrafilter is connected by a conduit to a blood storage container and the permeate or filtrate outlet of which ends in a filtrate line or in a filtrate collector vessel. The ultrafilter is located in a by-pass line to a blood storage container so that the patient's blood mixed with cardioplegic solution can be prepared to a hemoconcentrate after the perfusion has been completed. In the same manner, other blood removed by suction from the patient during the operation can be prepared by this by-pass line and the ultrafilter. Another pressure-controlled dosing pump sustains the first dosing pump and is connected to it in parallel.

13 Claims, 1 Drawing Figure

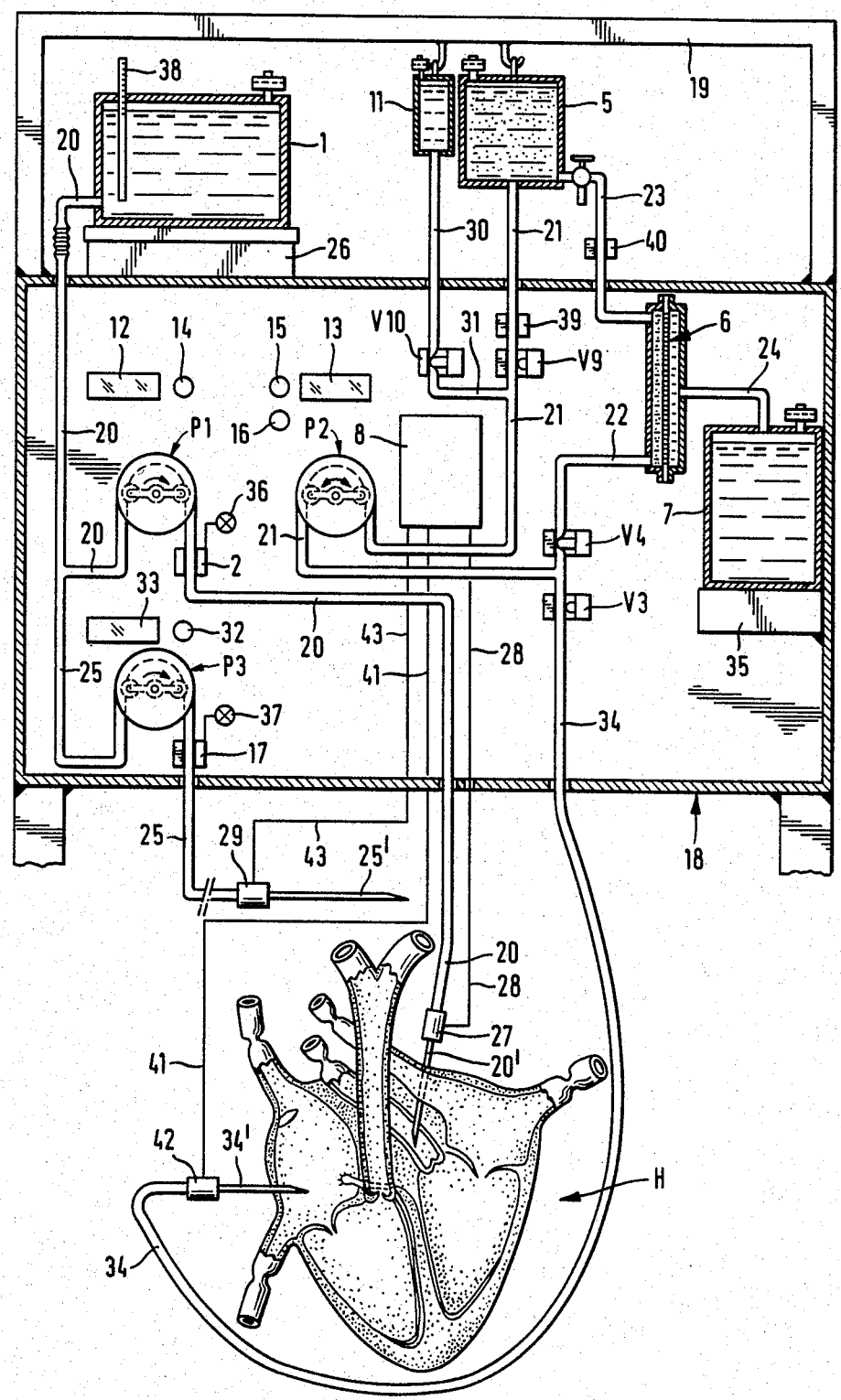

CARDIOPLEGIC CONTROLLING AND REGULATING SYSTEM

BACKGROUND OF THE INVENTION

The invention concerns a cardioplegic controlling and regulating device for dosed perfusing of cardioplegic perfusion solution, especially in open-heart operations. The device comprises a storage container for the cardioplegic solution which is connected by means of a fexible tubular line to the patient's heart and also comprises at least one pressure-controlled dosing pump which acts on the tubular line, as well as a take-off line which removes the blood mixed with the cardioplegic solution accumulated in the patient's heart and is dispensed into a suitable collector vessel.

Known devices of this type are used in an operating technique in open-heart surgery in which an artificially induced, reversible cardiac arrest is produced by perfusion of a cardioplegic solution. The blood in the coronary vessels of the heart is completely replaced in such a procedure by the perfused cardioplegic solution. The exchange of the blood by the cardioplegic solution is performed by at least one catheter introduced into certain areas of the heart for supplying the cardioplegic solution and by at least one catheter for removing the blood which is mixed and enriched with cardioplegic solution in accordance with the progress of the perfusion process.

The medical and technical background is treated in "Myocardial 'Equilibration Processes' and Myocardial Energy Turnover during Initiation of Artificial Cardiac Arrest with Cardioplegic Solution-Reasons for a Sufficiently Long Cardioplegic Perfusion", published in Thoraci Cardiovascular, Surgeon, 1981, pp. 71-6. Note also sources 1 to 29 cited in this article.

State-of-the-art devices are known which operate with one or with two pressure-controlled dosing pumps. Both the systems with a single pressure-controlled pump and also systems incorporating two pressure-controlled pumps have the following disadvantages from a medical and a technical viewpoint:

1. The preparation time until the cardiac arrest is too long, so that the patient is put under unnecessary strain.
2. The cardiac arrest time available for the actual open-heart surgery is too short, so that protracted and complicated operations can not be performed and simple operations which suddenly develop complications must be terminated too soon.
3. The actual perfusion is not as stress-free from a medical viewpoint as the condition of the patient actually requires.
4. The heart surgeon can exercise no regulating influence in the known devices in phase A, in which the cardiac arrest is achieved or in phase B, in which the perfusion must be completed by a reduced pump volume and a reduced pressure.
5. The patient's blood from the coronary vessels which accumulates during the operation (approximately 1 liter) is disposed of due to its being mixed with the cardioplegic solution and the possibility of an embolism after the end of the perfusion process, since the previously known cardioplegic controlling and regulating systems have no facilities for returning to the patient the blood which was withdrawn from him and is now mixed with the cardioplegic solution. This is at the expense of the patient and is unsatisfactory due to the lack of a technical solution.

SUMMARY OF THE INVENTION

The invention therefore has the task of improving a cardioplegic controlling and regulating system of the type claimed with simple means in such a manner that a perfusion which puts little stress on the heart from a medical viewpoint is possible, and that the system takes into account the various surgical techniques on an open heart and other inner organs and makes it possible to reuse the blood removed from the patient's heart.

This task is solved in accordance with the invention by the features of the claims.

The cardioplegic controlling and regulating device of the invention makes possible a pressure-controlled perfusion of cardioplegic solution to the heart in order to bring about an easily reversible cardiac arrest. The perfusion, which is introduced by at least one pressure-controlled dosing pump, is supported by a synchronous removal of the mixture of blood and cardioplegic solution from the heart by suction and the collecting of this mixture in a special vessel. A hemoconcentration up to a desired hematocrit reading is accomplished by concentrating the vacuum drawn mixture of blood and cardioplegic solution by filtering off the cardioplegic solution with an ultrafilter. If two pressure-controlled dosing pumps are used in conjunction with a dosing pump operating as a suction pump, the device can be employed universally for all operation possible in open-heart surgery.

With the system of the invention cardiac arrest can be achieved within approximately 10 to 20 sec. and a duration of 4 to 5 hours for the cardiac arrest can be achieved, which is available as operating time for the surgery and does not result in damage to the heart. If required, the perfusion process and the subsequent resuscitation of the heart can be repeated several times if necessary for the operation.

BRIEF DESCRIPTION OF THE DRAWING

The concept of the invention is explained in an embodiment in the form of an equipment diagram shown in the drawing for open-heart surgery.

DETAILED DESCRIPTION OF THE INVENTION

The entire device is designated by 18 and consists of a perfusate storage container 1 which ends via its perfusate line 20 in a catheter 20' which can be introduced into the heart "H". Terminal switch 2 for the first dosing pump P1 is located in perfusate line 20. A second perfusate line 25 dispenses from perfusate line 20, which second line is loaded by another pressure-controlled dosing pump P3. This dosing pump P3 is also associated with a terminal switch 17. Perfusate line 25 also ends in a catheter 25'. Both perfusate line 20, 25 have pressure sensors 27 and 29 in the immediate vicinity of catheters 20', 25' which sensors are connected over electric leads 28, 43 to pressure control device 8 in device 18.

The determination of the amount of cardioplegic solution delivered is performed gravimetrically through scale 26 supporting storage container 1 in conjunction with a controlling and regulating circuit for pump P1 or for pumps P1 and P3. The determination of the amount can also be performed indirectly by determining the revolutions per minute of pumps P1 and P3 with calibrated tubular conduits.

Thermometer 38 indicates the temperature of the cardioplegic solution in storage container 1, which is approximately +4 to +6° C. for the operation methods used.

The perfusion occurs in two phases. Cardiac arrest is achieved in phase A, while in phase B the perfusion is completed with reduced volume and pressure. Cardiac arrest is recognized, for example, by evaluating the EKG signal, measuring the temperature of the heart or visually by the heart surgeon.

Suction pump P2 is constructed as a reversible pump and loads blood-perfusate line 21, 34 with which the blood from the coronary vessels of the heart "H" and the cardioplegic solution with which it is mixed is removed by suction and loads at the same time blood-perfusate line 21 running to blood storage vessel 5, ultrafilter 6 located in by-pass 22, 23 as well as irrigation line 30,30 which is in shunt with blood-perfusate line 21 with blood storage container 5 and which ends in storage vessel 11 for the irrigation solution. Vessels 5 and 11 are suspended from a holder 19. The individual line branches can be blocked by conventional electromagnetic valves V3, V4, V9 and V10. The lines, in as far as they are not electric lines 28,30, 41, are customary flexible tubular conduits, and the valves of simple compression are squeeze valves. Ultrafilter 6 is connected on the permeate side over filtrate line 24 to catch vessel 7 which is placed on bracket 35. Bracket 35 can also be constructed as a scale for a gravimetric determination of the filtrate, which scale would communicate with device 18 over suitable data lines (not shown).

Device 18 also has display indicator 12 for pump P1, display indicator 13 for pump P2 and display indicator 33 for pump P3 which indicate the amount delivered per time unit. An infinitely variable potentiometer 14 is associated with pump P1, two other potentiometers 15 and 16 with pump P2 and potentiometer 32 with pump P3.

Device 18 of the invention consists, for the problem of the task posed, of the two pumps P1 and P2, of which P1 has the task of perfusing cardioplegic solution through heart "H" at a preselected quantity to be dispensed. The introduction of the cardioplegic solution produces the reversible cardiac arrest. A pressure-measuring and regulating system 8 of a conventional type stops pump P1, which delivers the perfusate in perfusate line 20 to the heart H, when an adjustable pressure limit is exceeded giving an alarm. This is necessary in order to prevent irreversible damage to the heart caused by over-expansion. The delivery is constantly indicated on left display indicator 12 as shown in the drawing. The second pump P2 is constructed as a reversible pump and rotates synchronously to the first pump P1 during the perfusion process with an adjustable deviation of −20% to +100%; however, it can also be operated independently of pump P1. In a filling, filtering or free irrigation process, pump P2 rotates counterclockwise and delivers a blood-cardioplegic mixture or a physiological saline solution through ultrafilter 6 to blood storage vessel 5, depending on the respective valve positions. The delivery, corresponding to the pump rpm's is constatly indicated in right display, indicator 13.

In order to prevent air from being pumped into the heart "H" of the patient during the perfusion, the level of the cardioplegic solution in the drip chamber is monitored with ultrasonic air detectors which are coupled, for example, to or integrated into terminal switch 2 or 17 of pump P1 or P3, respectively. Signal lamps 36 and 37 are provided.

As concerns its circuitry and its control, the additional, pressure-controlled pump P3 is integrated into device 18 analagously to the method of operation of pump P1.

Catheter 34' and line 34 for suction pump P2 are likewise provided with pressure receiver 42 and connected over lead 41 to pressure control device 8.

A device 18 which is ready for operation is started by a free irrigation of ultrafilter 6. For this, valve V3 is closed, V4 is opened, V9 closed and V10 opened. Dosing pump P2 runs for approximately 4 minutes with 500 ml/min. in a counterclockwise rotation. The irrigation solution from storage vessel 11 thus flows through line 30, 31, line section 21, line 22, ultrafilter 6 and line 23 and is discarded before storage vessel 5 by interrupting line 23 at 5a. The irrigation has the sole purpose of moistening the filter medium. After this irrigation process device 18 is operationally ready for performing the actual perfusion, whereby the valve positions assume the blocking and pass positions shown in the representation.

In order to accomplish the perfusion, pressure-controlled pump P1 delivers cardioplegic solution from storage container 1 at the speed set at rotary potentiometer 14 through perfusate line 20 to heart "H". If air is in perfusate line 20, terminal switch 2 automatically cuts off pump P1.

Pump P2 runs in a clockwise rotation synchronously with the rotation of pump P1, whereby valve V3 is opened, V4 closed and V9 opened and V10 closed. The speed of pump P2 can be varied in relation to pump P1 from −20% to +100% over an infinitely variable potentiometer. The delivery is indicated in right display indicator 13. If pump P1 is set at "0", pump P2 also stops. Residual amounts of the blood-solution mixture can now be sucked out by pump P2 by setting the potentiometer for pump P2 from the "0" setting to any delivery amount.

The preparation of the patient's blood by the device described below is performed separately from the actual subsequent operation.

The mixture of blood and cardioplegic solution collected in blood storage vessel 5 is subjected to a filtration in ultrafilter 6. To this end valve V3 is closed, V4 and V9 are opened and V10 is closed. Pump P2 runs counterclockwise at the speed set on rotary potentiometer 16 and delivers the blood-solution mixture from storage container 5 to ultrafilter 6 and back to storage container 5. The blood is concentrated by multiple circulations, whereby the cardioplegic solution and additional substances separated from the blood are delivered into filtrate catch vessel 7. The hemoconcentration takes place until a certain hematocrit value is reached by hematocrit meter 40, e.g. by measuring the conductivity, the capacity or by optical density measuring.

In order to initiate a new irrigation process, valve V3 is closed, V4 opened, V9 closed and V10 opened, whereby pump P2 forces approximately 260 ml physiological saline solution from storage vessel 11 into ultrafilter 6 and the line system in order to move any residual blood from the hose system and ultrafilter 6 into blood storage vessel 5. Then, pump P2 stops according to a program and device 18 is operationally ready for another repetition of the entire process.

Both pumps P1 and P2 can be operated and regulated independently of one another by manual intervention over switches, wherby pumps P1 and P2 rotate in a clockwise direction. The delivery speed is indicated in the corresponding display indicator.

The patient's blood concentrated in blood storage container 5 can be returned to him during the course of the further treatment, e.g. at the end of the actual heart operation, e.g. by a heart-lung machine. The amount in question is 1 to 2 liters of blood which was removed from the coronary vessels of the patient's heart during the perfusion process.

Device 18 of the invention also has the function of concentrating the additional blood drained from the patient during an operation in the filtration circulatory system and of returning it to the patient as required. The expanded blood present in the heart-lung machine and in the oxygenator can be concentrated back to the original hemocrit value by the hemoconcentration.

The program course is basically monitored, controlled and regulated by a microcomputer integrated into device 18. The person operating device 18 can of course intervene manually by means of function switches.

The work method described concerns the replacement of blood in the heart by a cardioplegic solution with the aid of the device. On the other hand, the exchange of the cardioplegic solution for blood after the operation has been completed is performed by connecting the heart to the natural circulatory system of the patient. Due to its special composition, the cardioplegic perfusion solution is to be viewed as a medical infusion solution.

The described device is equally suited, for example, for operations on an open kidney, liver and lung and can also be used for the limited preservation of donor organs for subsequent transplantation as well as for regional perfusion, e.g. to dispense rather large doses of medicamemts, e.g. cytostatic drugs.

What is claimed is:

1. In a cardioplegic controlling and regulating system for cardioplegic perfusion solution, including a reservoir means for the cardioplegic solution, a first tubular conduit operatively coupled to the reservoir means and adapted to deliver cardioplegic solution to a patient's heart, at least one pressure-controlled dosing pump adapted to force cardioplegic solution through the first conduit, an exhaust conduit adapted to remove blood and cardioplegic solution from the patient's heart, and a blood collection vessel means, the exhaust conduit being operatively coupled to the blood collection vessel means, the improvement comprising a second pump which is constructed as an exhaust pump and is adapted to remove the blood and cardioplegic solution from the heart, the second pump being adapted to selectively operate synchronously or assynchronously within predetermined limits with the at least one dosing pump, an ultrafilter means operatively coupled to the exhaust conduit and adapted to separate the blood and the cardioplegic solution, a third conduit operatively coupled at one end there of the ultrafilter means and at the other end thereof to the blood collection vessel means, a filtration conduit operatively coupled at one end thereof to the permeate or filtrate outlet of the ultrafilter means and at the other end thereof operatively coupled to a filtrate receiving collection vessel.

2. The system of claim 1 wherein a third perfusion pump supplies a quantity of cardioplegic solution, the third perfusion pump being operatively connected in parallel to the at least one pressure-controlled dosing pump through another perfusion line.

3. The system of claim 1 wherein the speed of the second pump can be controlled and regulated within a range of $-20\%$ to $+100\%$ of the speed of the at least one pressure-controlled dosing pump.

4. The system according to claim 1 wherein pressure sensors are operatively connected to the first tubular conduit and are connected to a pressure regulating device, the pressure regulating device being operatively connected to the pressure-controlled dosing pump as well as to the exhaust pump to control the perfusion.

5. The system according to claim 1 wherein the second pump is a reversible pump operatively coupled to a fluid line forming a blood perfusate line having one end that is operatively coupled to the blood collection vessel means and another end operatively coupled to the exhaust conduit, the exhaust conduit being valved by a control valve so that when the control valve is closed, blood and cardioplegic solution removed by the second pump bypasses the ultrafilter means.

6. The system according to claim 1 further comprising a pressure sensor adapted to provide an electrical feedback signal to a pressure regulating device which controls the second pump, thereby preventing air from being exhausted from the heart area.

7. The system according to claim 5 further comprising an irrigation line having a valve, the irrigation line being operatively coupled between said blood perfusate line and an irrigation solution storage vessel.

8. The system according to claim 5 further comprising a hematocrit sensing means operatively coupled to said third conduit for measuring the hemoconcentration of the mixture of blood and cardioplegic solution after the mixture has been passed a plurality of times through the ultrafilter means in a closed circular line formed by the exhaust conduit the blood perfusate line, and the third conduit.

9. The system according to claim 8 wherein the filtrate receiving collection vessel is mounted on a scale for monitoring the filtrate collected in the filtrate receiving collection vessel.

10. The system according to claim 8 wherein the hematocrit sensing means is an optical sensor.

11. The system according to claim 8, wherein the hematocrit sensing means is an electrical conductivity meter.

12. The system according to claim 8 wherein the hematocrit sensing means is an electrical capacitance sensor.

13. The system according to claim 1 wherein the reservoir means for the cardioplegic solution is disposed on a weighing scale.

* * * * *